(12) United States Patent
Gobbi et al.

(10) Patent No.: US 8,067,598 B2
(45) Date of Patent: Nov. 29, 2011

(54) HETEROFUSED PIPERIDINES AS OREXIN ANTAGONISTS

(75) Inventors: Luca Gobbi, Oberwil BL (CH); Henner Knust, Rheinfelden (DE); Parichehr Malherbe, Muttenz (CH); Matthias Nettekoven, Grenzach-Wyhlen (DE); Emmanuel Pinard, Linsdorf (FR); Olivier Roche, Folgensbourg (FR); Mark Rogers-Evans, Oberwil BL (CH)

(73) Assignee: Hoffman-La Roche Inc., Nutley, NJ (US)

( * ) Notice: Subject to any disclaimer, the term of this patent is extended or adjusted under 35 U.S.C. 154(b) by 691 days.

(21) Appl. No.: 12/056,324

(22) Filed: Mar. 27, 2008

(65) Prior Publication Data
US 2008/0249125 A1   Oct. 9, 2008

(30) Foreign Application Priority Data

Apr. 4, 2007   (EP) .................................... 07105596

(51) Int. Cl.
C07D 471/04   (2006.01)
C07D 513/04   (2006.01)
A61K 31/4365   (2006.01)
A61K 31/437   (2006.01)
A61K 31/4375   (2006.01)

(52) U.S. Cl. .......... 546/87; 546/114; 546/122; 514/292; 514/300; 514/301

(58) Field of Classification Search .................. 546/114, 546/80, 122, 87; 514/292, 300, 301
See application file for complete search history.

(56) References Cited

FOREIGN PATENT DOCUMENTS
WO   WO 2004/085403   10/2004
WO   WO 2005/118548   12/2005
WO   WO 2007/105177   9/2007
WO   WO 2007/122591   11/2007

OTHER PUBLICATIONS

Ernest L. Eliel "Infelicitous Stereochemical Nomenclature" CHIRALITY 1997, 9, 428-430.*
Siegel, J. M., Annu. Rev. Psychol. vol. 55, pp. 125-148 (2004).
De Lecea et al., Proc. Natl. Acad. Sci. USA vol. 95, pp. 322-327 (1998).
Sakurai et al., Cell, vol. 92, pp. 573-585 (1998).
Sakurai, Regulatory Peptides, vol. 126 pp. 3-10 (2005).
Peyron et al., J. Neurosci. vol. 18, pp. 9996-10015 (1998).
Nambu et al., Brain Res. vol. 827, pp. 243-260 (1999).
Chemelli et al., Cell, vol. 98 pp. 437-451 (1999).
Lin et al., Cell, vol. 98, pp. 365-376 (1999).
Nishino et al., Lancet, vol. 355, pp. 39-40 (2000).
Peyron et al., Nature Medicine vol. 6, pp. 991-997 (2000).
Mignot et al., Sleep vol. 11, pp. 1012-1020 (1997).
Piper et al., Eur. J. Neuroscience vol. 12, pp. 726-730 (2000).
Sakamoto et al., Regul. Pept. vol. 118, pp. 183-191 (2004).
Ida et al., Biochem. Biophys. Res. Comm. vol. 270, pp. 318-323 (2000).
Kuru et al., Neuroreport vol. 11 pp. 1977-1980 (2000).
Winsky-Sommerer et al., J. Neuroscience vol. 24 pp. 11439-11448 (2004).
Chang et al., Neuroscience Research vol. 57, Issue 3, pp. 462-466 (2007).
Suzuki et al., Brain Research vol. 1044 pp. 116-121 (2005).
Digby et al, J. Endocrinol. vol. 191 pp. 129-136 (2006).
Cai et al., Expert Opin. Ther. Patents, vol. 16(5) pp. 631-646 (2006).
Bingham et al., Current Opin. in Drug Discovery & Development vol. 9(5) pp. 551-559 (2006).
Bourgin et al., J. Neurosci. vol. 20(20), pp. 7760-7765 (2000).
Smith et al., Neurosci. Lett. vol. 341(3) pp. 256-258 (2003).
Malherbe et al., Mol. Pharmacol. vol. 64 pp. 823-832 (2003).
Shiozawa et al., Chemical & Pharmaceutical Bulletin, vol. 32(7) pp. 2522-2529 (1984).
Iriarte et al., Journal of Heterocyclic Chemistry (1976) vol. 13(2) pp. 393-394.
Brisbare-Roch, C. et al, *Nature Medicine*, 12(2) (2007) 150-155 XP002483450.

* cited by examiner

*Primary Examiner* — David K O Dell
(74) *Attorney, Agent, or Firm* — Goerge W. Johnston; Patricia S. Rocha-Tramaloni; Kimberly J. Prior

(57) ABSTRACT

The present invention relates to compounds of formula

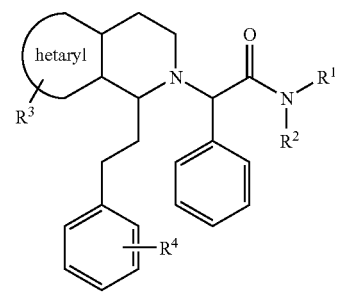

I wherein $R^1$, $R^2$, $R^3$, and $R^4$ are as defined herein and
hetaryl is a one or two ring-membered heteroaromatic ring system, connected to the carbon atoms of the piperidine group selected from the group consisting of

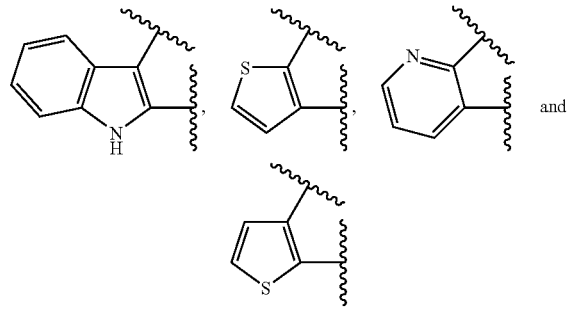

or to pharmaceutically suitable acid addition salts, optically pure enantiomers, racemates or diastereomeric mixtures thereof. These compounds are orexin receptor antagonists and may be useful in the treatment of disorders in which orexin pathways are involved, like sleep disorders.

9 Claims, No Drawings

HETEROFUSED PIPERIDINES AS OREXIN ANTAGONISTS

PRIORITY TO RELATED APPLICATION(S)

This application claims the benefit of European Patent Application No. 07105596.6, filed Apr. 4, 2007, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al., *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al., *Cell*, 98, 365-376, 1999), (c) lack of OX-A and OX-B was observed in human narcoleptic patients (Nishino et al., *Lancet*, 355, 39-40, 2000; Peyron et al., *Nature Medicine*, 6, 991-997, 2000), (d) it has been shown that Modafinil, an anti-narcoleptic drug with unknown mechanism of action, activates orexin neurons (Mignot et al., *Sleep*, 11, 1012-1020, 1997; Chemelli et al., *Cell*, 98, 437-451, 1999). The intracerebroventricular (icv) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al., *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R(N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., *Neurosci Res.*, 21 Dec. 2006). A recent preclinical report (Suzuki et al., *Brain Research*, 1044, 116-121, 2005) has suggested an anxiogenic effect of OX-A. The icv injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

Numerous documents describe the current knowledge on orexin pathway, for example the following documents:
Expert Opin. Ther. Patents (2006), 16(5), 631-646
Current Opinion in Drug Discovery & Development, 2006, 9(5), 551-559
J. Neurosci (2000), 20(20), 7760-7765
Neurosci Lett, (2003), 341(3), 256-258

SUMMARY OF THE INVENTION

The present invention provides compounds of formula I

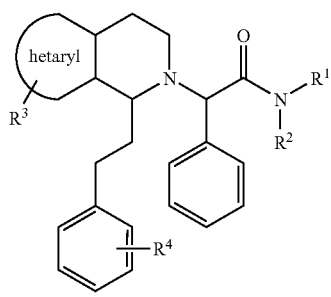

wherein
$R^1$ and $R^2$ are each independently hydrogen or lower alkyl;
$R^3$ is hydrogen, halogen, lower alkyl, lower alkyl substituted by halogen, lower alkoxy or lower alkoxy substituted by halogen;
$R^4$ is halogen, lower alkyl, lower alkyl substituted by halogen, lower alkoxy or lower alkoxy substituted by halogen; and
hetaryl is a one or two ring-membered heteroaromatic ring system, connected to the carbon atoms of the piperidine group selected from the group consisting of

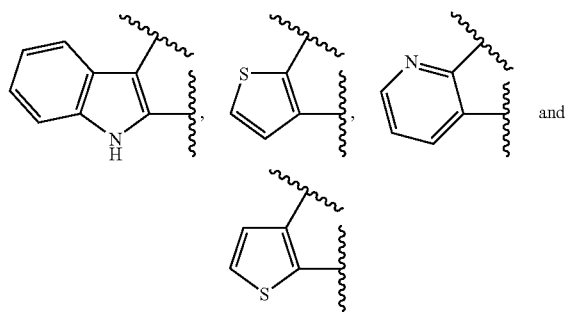

or pharmaceutically suitable acid addition salts, optically pure enantiomers, racemates or diastereomeric mixtures thereof.

The compounds of formula I are novel. The advantage over orexin receptor antagonists described in the literature is an improvement of physicochemical/DMPK profile which is an important aspect in the development as drug.

Compounds of formula I are orexin receptor antagonists and may be useful in the treatment of disorders, in which orexin pathways are involved like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like.

The term "lower alkoxy" denotes an alkyl group as defined above, which is attached via an oxygen atom.

The term "halogen" denotes chlorine, iodine, fluorine and bromine.

The term "cycloalkyl" denotes a saturated carbocyclic group, containing 3-6 carbon atoms.

The term "heterocycloalkyl" denotes a non aromatic radical having one or more rings that contains one, two, or three ring heteroatoms selected from N, O, and S, for example oxetanyl, tetrahydrofuranyl, tetrahydropyranyl, azetidinyl; pyrrolidinyl, piperidinyl, piperazinyl, morpholinyl, thiomorpholinyl.

The term "aryl" means the monovalent cyclic aromatic hydrocarbon group consisting of one or more fused rings in which at least one ring is aromatic in nature. Examples of aryl radicals include, but are not limited to, phenyl, naphthyl, biphenyl, indanyl, anthraquinolyl, and the like.

"Heteroaryl" means the monovalent aromatic group having one or more rings containing one, two, or three heteroatoms within the ring (chosen from nitrogen, oxygen, or sulfur). Examples of heteroaryl radicals include, but are not limited to, imidazolyl, oxazolyl, isoxazolyl, thiazolyl, thiophenyl, furanyl, pyridinyl, pyrazinyl, pyrimidinyl, pyridazinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphthyridinyl, and the like.

The term "heterocyclic ring, optionally containing further ring-heteroatoms selected from N, O and S" means a non-aromatic ring containing one N-atom, optionally containing one or more additional heteroatoms selected from O, N and S, for example pyrrolin-1-yl, piperidin-1-yl, azepin-1-yl, piperazin-1-yl, morpholin-4-yl, thiomorpholin-4-yl, 1-oxo-thiomorpholin-4-yl or 1,1-dioxo-thiomorpholin-4-yl.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein the term "hetaryl" denotes a one or two ring-membered heteroaromatic ring system, connected to the carbon atoms of the piperidine group and containing one or more heteroatoms, selected from N, S and O", for example the groups

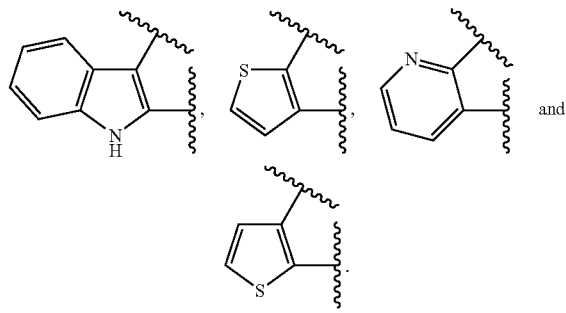

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those, wherein one of $R^1$ or $R^2$ is hydrogen and the other is lower alkyl.

A preferred group of these compounds are those, wherein hetaryl is

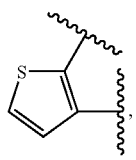

for example the following compounds:
N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2);
N-methyl-2-{2-methyl-4-[2-(4-trifluoromethyl-phenyl)-ethyl]-6,7-dihydro-4H-thieno[3,2-c]pyridin-5-yl}-2-phenyl-acetamide (enantiomer 2);
2-{4-[2-(4-methoxy-phenyl)-ethyl]-2-methyl-6,7-dihydro-4H-thieno[3,2-c]pyridin-5-yl}-N-methyl -2-phenyl-acetamide (diastereoisomer 2);
2-{4-[2-(4-methoxy-phenyl)-ethyl]-2-methyl-6,7-dihydro-4H-thieno[3,2-c]pyridin-5-yl}-N-methyl -2-phenyl-acetamide (enantiomer 1);
2-{4-[2-(4-methoxy-phenyl)-ethyl]-2-methyl-6,7-dihydro-4H-thieno[3,2-c]pyridin-5-yl}-N-methyl -2-phenyl-acetamide (enantiomer 2);
2-{4-[2-(4-methoxy-phenyl)-ethyl]-2,3-dimethyl-6,7-dihydro-4H-thieno[3,2-c]pyridin-5-yl}-N-methyl -2-phenyl-acetamide (diastereoisomer 2);
2-{4-[2-(4-methoxy-phenyl)-ethyl]-2,3-dihydro-4H-thieno[3,2-c]pyridin-5-yl}-N-methyl -2-phenyl-acetamide (enantiomer 1);
2-{4-[2-(4-methoxy-phenyl)-ethyl]-2,3-dimethyl-6,7-dihydro-4H-thieno[3,2-c]pyridin-5-yl}-N-methyl -2-phenyl-acetamide (enantiomer 2);
2-{2-chloro-4-[2-(4-methoxy-phenyl)-ethyl]-6,7-dihydro-4H-thieno[3,2-c]pyridin-5-yl}-N-methyl -2-phenyl-acetamide (diastereoisomer 2); and
2-{2-chloro-4-[2-(4-methoxy-phenyl)-ethyl]-6,7-dihydro-4H-thieno[3,2-c]pyridin-5-yl}-N-methyl -2-phenyl-acetamide (enantiomer 1).

A further preferred group of these compounds are further those, wherein hetaryl is

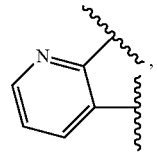

for example the compounds
2-{5-[2-(4-methoxy-phenyl)-ethyl]-7,8-dihydro-5H-[1,6]naphthyridin-6-yl}-N-methyl-2-phenyl-acetamide (diastereoisomer 2);
2-{5-[2-(4-Methoxy-phenyl)-ethyl]-7,8-dihydro-5H-[1,6]naphthyridin-6-yl}-N-methyl-2-phenyl-acetamide (enantiomer 2);
2-{5-[2-(3-Methoxy-phenyl)-ethyl]-7,8-dihydro-5H-[1,6]naphthyridin-6-yl}-N-methyl-2-phenyl-acetamide (diastereoisomer 2);
2-{5-[2-(3-Methoxy-phenyl)-ethyl]-7,8-dihydro-5H-[1,6]naphthyridin-6-yl}-N-methyl-2-phenyl-acetamide (enantiomer 2);
N-Methyl-2-phenyl-2-{5-[2-(4-trifluoromethyl-phenyl)-ethyl]-7,8-dihydro-5H-[1,6]naphthyridin-6-yl}-acetamide (diastereoisomer 2); and
2-{5-[2-(4-Fluoro-phenyl)-ethyl]-7,8-dihydro-5H-[1,6]naphthyridin-6-yl}-N-methyl-2-phenyl-acetamide (enantiomer 2).

A further preferred group of these compounds are those, wherein hetaryl is

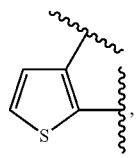

for example the compound
N-methyl-2-phenyl-2-{7-[2-(4-trifluoromethyl-phenyl)-ethyl]-4,7-dihydro-5H-thieno[2,3-c]pyridin-6-yl}-acetamide (diastereoisomer 2).

One embodiment of the present invention are compounds of formula IA

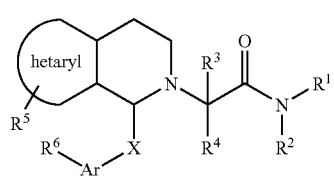

IA wherein $R^1$ and $R^2$ are each independently hydrogen, lower alkyl, lower alkyl substituted by halogen, —(CH$_2$)$_o$—O-lower alkyl, —(CH$_2$)$_o$—N-(lower alkyl)$_2$, (CH$_2$)$_p$-cycloalkyl, (CH$_2$)$_p$-heterocycloalkyl, (CH$_2$)$_p$-aryl, or (CH$_2$)$_p$-heteroaryl, which rings are optionally substituted by R, or $R^1$ and $R^2$ together with the N-atom to which they are attached form a heterocyclic ring, optionally containing further ring-heteroatoms selected from N, O and S;

R is lower alkyl, lower alkoxy, halogen or lower alkyl substituted by halogen;

$R^3$ is lower alkyl, lower alkyl substituted by halogen, cycloalkyl, heterocycloalkyl, unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, SO$_2$-lower alkyl and —NR$^1$R$^2$;

$R^4$ is hydrogen or lower alkyl;

$R^5$ and $R^6$ are each independently one or more substituents selected from the group consisting of hydroxy, halogen, lower alkyl, lower alkyl substituted by halogen, lower alkoxy, lower alkoxy substituted with halogen, nitro, cyano, SO$_2$-lower alkyl and —NR$^1$R$^2$;

Ar is unsubstituted or substituted aryl or heteroaryl and wherein the aryl and the heteroaryl groups are optionally substituted by one or more substituents as defined by $R^5$ and $R^6$;

X is —(CR$^7$R$^8$)$_n$—;

$R^7$ and $R^8$ are each independently hydrogen or lower alkyl;

n is 0, 1, 2 or 3;

o is 2 or 3; and p is 0, 1 or 2;

or pharmaceutically suitable acid addition salts, optically pure enantiomers, racemates or diastereomeric mixtures thereof.

The present compounds of formula I and their pharmaceutically acceptable salts can be prepared by methods known in the art, for example, by processes described below, which process comprises transforming a compound of formula

V and a compound of formula

VI with an activating agent
to obtain a compound of formula

I wherein the substituents are as described above, and if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

II

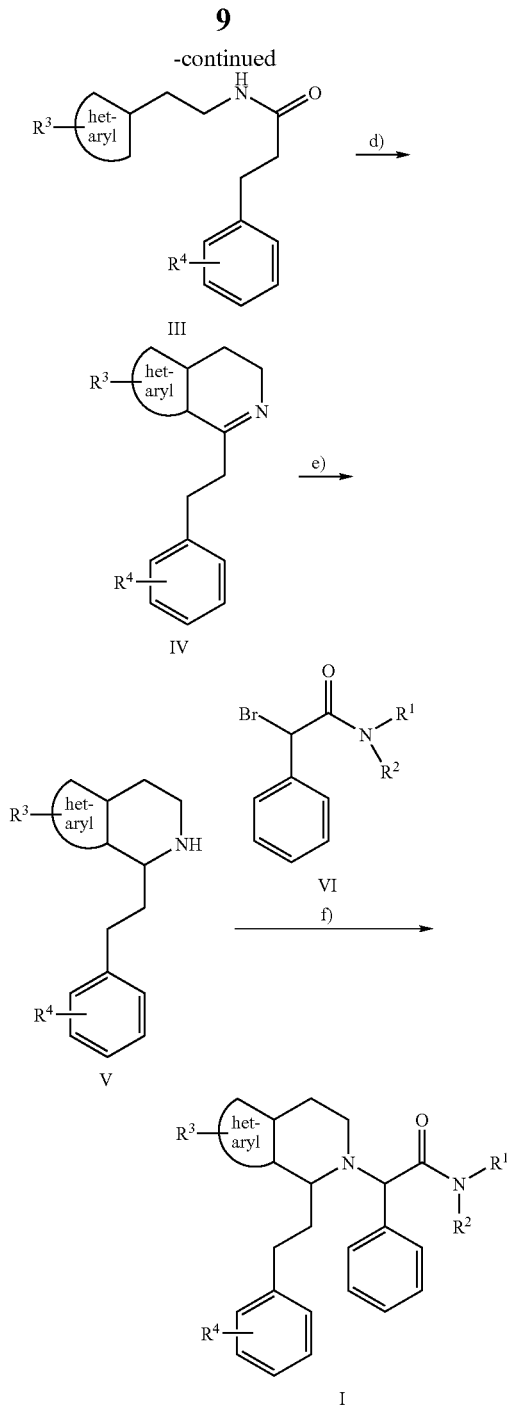

Compounds of formula II are commercial available or may be prepared by step a) or b). The substituents are as described above.

Amine derivatives II can be commercially available or can be synthesised by various methods as described in literature. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999).

Step a)

However, it is convenient to transform a suitable aldehyde under basic conditions with nitromethane to the α,β-unsaturated nitro-derivative.

Step b)

This nitro-derivative can be reduced to the respective amine derivative II under suitable conditions, namely depending on the nature of the nitro-derivative.

Step c)

Coupling of amine derivatives II with suitable acids can be achieved by various methods. However, it is convenient to react amine derivative II with acid derivatives in the presence of a coupling reagent, a base and a solvent. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives III.

Step d)

Amide derivatives III can be cyclised to access di-hydro compounds IV under various conditions. However, we find it convenient to cyclise amide derivative in the presence of POCl₃ in the presence or absence of a solvent. There is no particular restriction on the nature of the solvent to be employed, provided that it has no adverse effect on the reaction or the reagents involved and that it can dissolve the reagents, at least to some extent. Examples for suitable solvents include: acetonitrile, dioxane, THF, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield di-hydro derivatives IV.

Step e)

Di-hydro derivatives IV can be transformed to the respective tetrahydro derivatives V under reducing conditions. Reduction can be achieved by various methods as described in literature. However, it is convenient to react Di-hydro derivatives IV with a reducing agent in the presence of a solvent. For example sodium borohydride (NaBH₄) and the like can equally well be employed to affect such transformation. We find it convenient to carry out the reaction in a solvent like ethanol. There is no particular restriction on the nature of the solvent to be employed, provided that it has no adverse effect on the reaction or the reagents involved and that it can dissolve the reagents, at least to some extent. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield tetrahydro derivatives V.

Step f)

Tetrahydro derivatives V can be transformed to the respective heterocyclic derivatives I under various conditions. Reaction of tetrahydro derivatives V with a corresponding Br-acetamide derivative VI (either commercially available, or synthesized from commercially available starting materials, as appropriate) in the presence of a solvent and a base and optionally other activating agents directly give access to heterocyclic derivatives I. We find it convenient to carry out the reaction in a solvent like acetonitrile or DMF, dioxane and the like. There is no particular restriction on the nature of the solvent to be employed, provided that it has no adverse effect on the reaction or the reagents involved and that it can dissolve the reagents, at least to some extent. There is no particular restriction on the nature of the base used in this stage, and any base commonly used in this type of reaction may equally be employed here. Examples of such bases include triethylamine and diisopropylethylamine, and the like. There is no particular restriction on the nature any optionally used activating agent in this stage, and any agent commonly used in this type of reaction may equally be employed here. Examples of such agents include sodium iodide, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield heterocyclic derivatives I. Optionally, heterocyclic derivatives I can be accessed through reaction of tetrahydro derivatives V with, for example ethylbromophenylacetate, intermediately accessing the respective ester derivative which can be transformed under acidic or basic aqueous conditions to the respective acid derivatives which subsequently can be transformed to the final heterocyclic derivatives through reaction with an amine under coupling conditions. The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The intermediately built acid can conveniently be transformed to the respective amide through coupling with an amine (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield heterocyclic derivatives I.

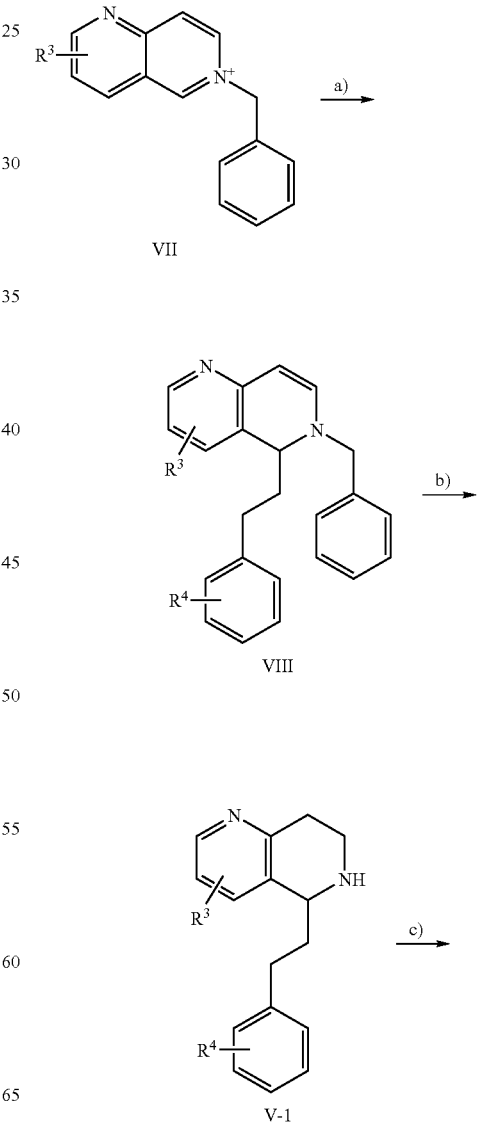

Scheme 2

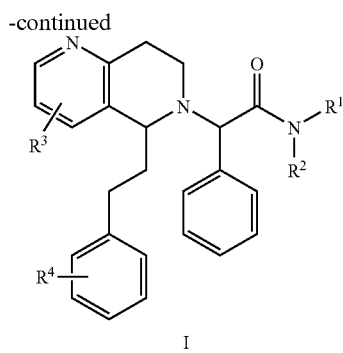

Compounds of formula I for which hetaryl is a pyridine group can be prepared according to scheme 2.

Step a)

Substituted 6-benzyl-[1,6]naphthyridin-6-ium bromide derivative VII (Chemical & Pharmaceutical Bulletin, 32(7), 2522-9; 1984) can be reacted with a Grignard reagent to provide 6-benzyl-5,6-dihydro-[1,6]naphthydrine VIII.

Step b)

VIII can be hydrogenated with Palladium on charcoal under hydrogen to provide 5,6,7,8-tetrahydro-[1,6]naphthyridine V-1.

Step c)

A compound of formula V-1 can be alkylated with a compound of formula VI as described in scheme 1 above to provide a compound of formula I.

The compounds were investigated in accordance with the test given hereinafter.

Intracellular $Ca^{2+}$ Mobilization Assay

The Chinese Hamster Ovary (dHFr-) mutant cell line stably expressing human orexin-1 (hOX1) or human orexin-2 (hOX2) receptors were maintained in Dulbecco's Modified Eagle Medium (1X) with GlutaMax™ 1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 μg/ml penicillin and 100 μg/ml streptomycin. The cells were seeded at $5 \times 10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 μM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10X) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., *Mol. Pharmacol.*, 64, 823-832, 2003). Orexin A (catalog No. 1455, Toris Cookson Ltd, Bristol, UK) was used as agonist. Orexin A (50 mM stock solution in DMSO) was diluted in FLIPR buffer+0.1% BSA. The $EC_{50}$ and $EC_{80}$ values of orexin-A were measured daily from standard agonist concentration-response curves in CHO(dHFr-)-OX1R and -OX2R cell lines. All compounds were dissolved in 100% DMSO. Inhibition curves were determined by addition of 11 concentrations (0.0001-10 μM) of inhibitory compounds and using $EC_{80}$ value of orexin-A as agonist (a concentration which gave 80% of max agonist response, determined daily).

The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{nH})$, where nH=slope factor using Excel-fit 4 software (Microsoft).

$K_b$ values were calculated according to the following equation $K_b=IC_{50}/(1+[A]/EC_{50})$ where A is the concentration of agonist added which is very close to agonist $EC_{80}$ value, and $IC_{50}$ and EC50 values were derived from the antagonist inhibition and orexin-A or B agonist curves, respectively.

Representative compounds show a $K_b$ value (μM) in human on orexin receptor as shown in the table below.

| Example | $K_b$ (μM) OX2R (human) | $K_b$ (μM) OX1R (human) |
|---|---|---|
| 4 | 0.0204 | 0.047 |
| 6 | 0.0091 | 0.0401 |
| 7 | 0.0266 | 0.0311 |
| 8 | 0.0075 | 0.0135 |
| 9 | 0.0566 | 0.4084 |
| 11 | 0.0215 | 0.1639 |
| 13 | 0.005 | 0.0402 |
| 14 | 0.0036 | 0.0221 |
| 15 | 0.0169 | 0.4081 |
| 16 | 0.0148 | 0.0524 |
| 17 | 0.0462 | 0.0162 |
| 18 | 0.032 | 0.0095 |
| 22 | 0.038 | 0.1045 |
| 23 | 0.0852 | 0.2227 |
| 25 | 0.0296 | 0.1085 |
| 26 | 0.0356 | 0.3484 |
| 28 | 0.0601 | 0.3006 |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants.

They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item Ingredients | 5 mg | 25 mg | 100 mg | 500 mg |
| 1. Compound of formula I | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item Ingredients | 5 mg | 25 mg | 100 mg | 500 mg |
| 1. Compound of formula I | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

In the examples described below the following abbreviations have been used:

CDI=N,N'-carbonyldiimidazole
DCC=N,N'-dicyclohexylcarbodiimide
EDCI=1-(3-dimethylaminopropyl)-3-ethylcarbodiimide hydrochloride
HATU=1-[bis(dimethylamino)methylene]-1H-1,2,3-triazolo[4,5-b]pyridinium-3-oxide hexafluorophosphate
HOBT=1-hydroxy-1,2,3-benzotriazole
TBTU=O-benzotriazol-1-yl-N,N,N',N'-tetramethyluronium tetrafluoroborate
DMF=dimethylformamide
DCM=dichloromethane

EXAMPLE 1

2-{6-Methoxy-1-[2-(4-trifluoromethyl-phenyl)-ethyl]-1,3,4,9-tetrahydro-β-carbolin-2-yl}-N-methyl - 2-phenyl-acetamide (diastereoisomer 1)

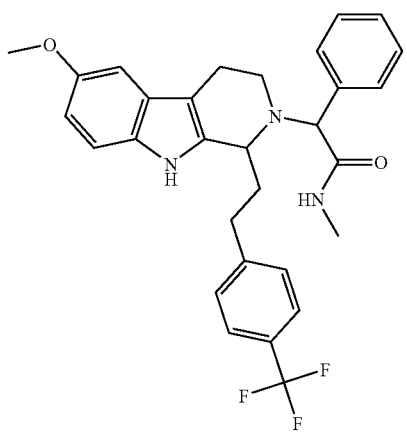

a) step 1:

N-[2-(5-Methoxy-1H-indol-3-yl)-ethyl]-3-(4-trifluoromethyl-phenyl)-propionamide

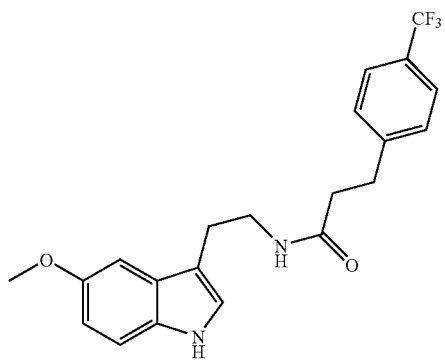

A mixture of 0.3 g (1.57 mmol) 5-methoxytryptamine, 0.34 g (1.57 mmol) 4-(trifluoromethyl)hydrocinnamic acid (commercially available), 0.6 g (1.8 mmol) TBTU and 0.6 g (4.6 mmol) DIPEA in 6 mL DMF was shaken for 3 h at room temperature. 50 mL water was added and the mixture was extracted with DCM. The combined organic phases were washed with water, dried with $MgSO_4$ and evaporated to dryness to yield the title compound which was used without further purification in the consecutive step.

MS(m/e): 391.1 (MH$^+$).

b) step 2:

6-Methoxy-1-[2-(4-trifluoromethyl-phenyl)-ethyl]-4,9-dihydro-3H-β-carboline

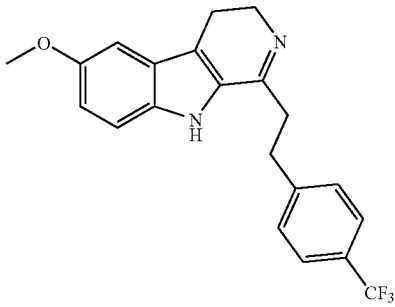

A mixture of 0.61 g (1.57 mmol) N-[2-(5-methoxy-1H-indol-3-yl)-ethyl]-3-(4-trifluoromethyl-phenyl)-propionamide and 1 mL $POCl_3$ in 2.5 mL acetonitrile was heated to reflux for 16 h. Water was added and the mixture was subjected to purification by preparative HPLC on reversed phase eluting with a gradient formed from acetonitrile, water and formic acid. The combined product fractions were evaporated to dryness to yield 0.09 g (15%) of the title compound as yellow crystals.

MS(m/e): 373.1 (MH$^+$).

c) step 3:

6-Methoxy-1-[2-(4-trifluoromethyl-phenyl)-ethyl]-2,3,4,9-tetrahydro-1H-β-carboline

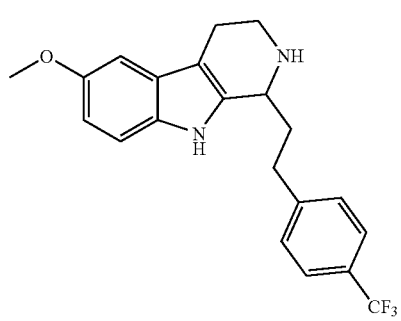

A mixture of 91 mg (0.24 mmol) 6-methoxy-1-[2-(4-trifluoromethyl-phenyl)-ethyl]-4,9-dihydro-3H-β-carboline and 27.7 mg (0.73 mmol) sodium borohydride in 5 mL ethanol was stirred for 2 h at room temperature. The mixture was filtered and evaporated to dryness. Trituration with ethyl acetate yielded after drying 90 mg (98%) of the title compound as light yellow solid.

MS(m/e): 375.4 (MH$^+$).

d) step 4:

{6-Methoxy-1-[2-(4-trifluoromethyl-phenyl)-ethyl]-1,3,4,9-tetrahydro-β-carbolin-2-yl}-phenyl-acetic acid ethyl ester (diastereoisomer 1 and diastereoisomer 2)

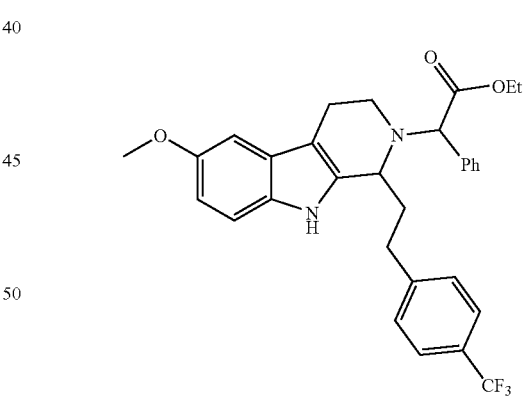

A mixture of 90 mg (0.24 mmol) 6-methoxy-1-[2-(4-trifluoromethyl-phenyl)-ethyl]-2,3,4,9-tetrahydro-1H-β-carboline, 59 mg (0.24 mmol) ethyl bromophenylacetate and 28.8 mg (0.27 mmol) $Na_2CO_3$ in 4 mL methanol was heated to reflux for 16 h. After filtration DMF was added and the mixture was subjected to purification by preparative HPLC on reversed phase eluting with a gradient formed from acetonitrile, water and formic acid. The combined product fractions were evaporated to dryness to yield 21 mg (16%) {6-methoxy-1-[2-(4-trifluoromethyl-phenyl)-ethyl]-1,3,4,9-tetrahydro-β-carbolin-2-yl}-phenyl-acetic acid ethyl ester (diastereoisomer 1)

(MS(m/e): 537.3 (MH⁺)) and 10 mg (7%) {6-methoxy-1-[2-(4-trifluoromethyl-phenyl)-ethyl]-1,3,4,9-tetrahydro-β-carbolin-2-yl}-phenyl-acetic acid ethyl ester (diastereoisomer 2)

(MS(m/e): 537.3 (MH⁺))

e) step 5:

{6-Methoxy-1-[2-(4-trifluoromethyl-phenyl)-ethyl]-1,3,4,9-tetrahydro-carbolin-2-yl}-phenyl-acetic acid (diastereoisomer 1)

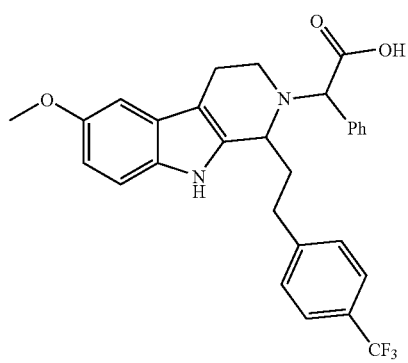

A mixture of 21 mg (0.03 mmol) {6-methoxy-1-[2-(4-trifluoromethyl-phenyl)-ethyl]-1,3,4,9-tetrahydro-β-carbolin-2-yl}-phenyl-acetic acid ethyl ester (diastereoisomer 1), 2.3 mg (0.09 mmol) LiOH.H₂O in water, methanol and THF was stirred at 40° C. for 16 h. 50 uL 4N KOH aq. was added and stirring was continued at 45° C. for 4 h. The mixture was acidified with HCL aq. and subjected to purification by preparative HPLC on reversed phase eluting with a gradient formed from acetonitrile, water and formic acid. The combined product fractions were evaporated to dryness to yield 19.6 mg (98%) of the title compound as off white solid.

MS(m/e): 509.1 (MH⁺).

f) step 6:

2-{6-Methoxy-1-[2-(4-trifluoromethyl-phenyl)-ethyl]-1,3,4,9-tetrahydro-β-carbolin-2-yl}-N-methyl -2-phenyl-acetamide (diastereoisomer 1)

A mixture of 9.8 mg (0.02 mmol) {6-methoxy-1-[2-(4-trifluoromethyl-phenyl)-ethyl]-1,3,4,9-tetrahydro-carbolin-2-yl}-phenyl-acetic acid (diastereoisomer 1), 196 uL 2M methylamine (0.39 mmol) in THF, 8.2 mg (0.025 mmol) TBTU in 1 mL DMF was shaken for 16 h at room temperature. Formic acid was added and the mixture was subjected to purification by preparative HPLC on reversed phase eluting with a gradient formed from acetonitrile, water and formic acid. The combined product fractions were evaporated to dryness to yield 2.2 mg (22%) of the title compound as off white solid.

MS(m/e): 522.5 (MH⁺).

EXAMPLE 2

2-{6-Methoxy-1-[2-(4-trifluoromethyl-phenyl)-ethyl]-1,3,4,9-tetrahydro-β-carbolin-2-yl}-N-methyl -2-phenyl-acetamide (diastereoisomer 2)

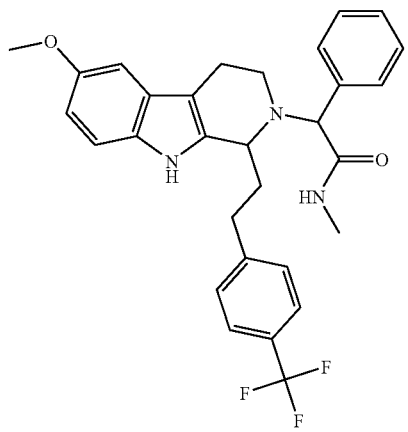

a) step 1:

{6-Methoxy-1-[2-(4-trifluoromethyl-phenyl)-ethyl]-1,3,4,9-tetrahydro-carbolin-2-yl}-phenyl-acetic acid (diastereoisomer 2)

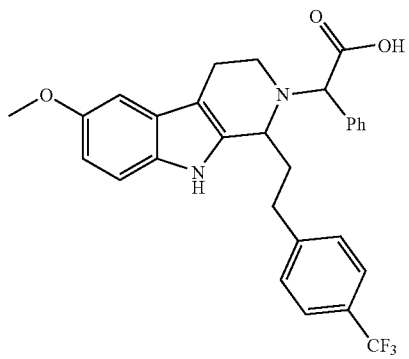

A mixture of 10 mg (0.018 mmol) {6-methoxy-1-[2-(4-trifluoromethyl-phenyl)-ethyl]-1,3,4,9-tetrahydro-β-3-carbolin-2-yl}-phenyl-acetic acid ethyl ester (diastereoisomer 2), 1.1 mg (0.04 mmol) LiOH.H₂O in water, methanol and THF was stirred at 40° C. for 16 h. 50 uL 4N KOH aq. was added and stirring was continued at 45° C. for 4 h. The mixture was acidified with HCL aq. and subjected to purification by preparative HPLC on reversed phase eluting with a gradient formed from acetonitrile, water and formic acid. The combined product fractions were evaporated to dryness to yield the title compound as off white solid.

MS(m/e): 509.3 (MH⁺).

b) step 2:

2-{6-Methoxy-1-[2-(4-trifluoromethyl-phenyl)-ethyl]-1,3,4,9-tetrahydro-3-carbolin-2-yl}-N-methyl -2-phenyl-acetamide (diastereoisomer 2)

A mixture of 10 mg (0.02 mmol) {6-methoxy-1-[2-(4-trifluoromethyl-phenyl)-ethyl]-1,3,4,9-tetrahydro-carbolin- 2-yl}-phenyl-acetic acid (diastereoisomer 2), 196 uL 2M methylamine (0.39 mmol) in THF, 8.2 mg (0.025 mmol) TBTU in 1 mL DMF was shaken for 16 h at room temperature. Formic acid was added and the mixture was subjected to purification by preparative HPLC on reversed phase eluting with a gradient formed from acetonitrile, water and formic acid. The combined product fractions were evaporated to dryness to yield 1.1 mg (11%) of the title compound as off white solid.

MS(m/e): 522.4 (MH$^+$).

EXAMPLE 3 AND EXAMPLE 4

N-Methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and N-Methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2)

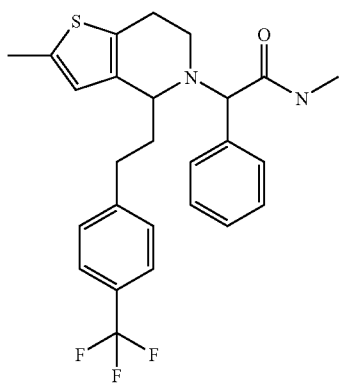

Example 3: diastereoisomer 1
Example 4: diastereoisomer 2 a) step 1:

2-Methyl-5-((E)-2-nitro-vinyl)-thiophene

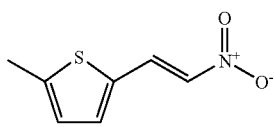

A solution of 10.3 g (80 mmol) 5-methyl-2-thiophenecarboxaldehyde (commercially available) and 13.5 mL nitromethane in 160 mL methanol was cooled to −5° C. A 50% sodium hydroxide solution (80 mL) was added drop wise maintaining the temperature between 5 and 10° C. (formation of a yellow precipitate). After complete addition the mixture was stirred at 10° C. for 1 h. The suspension was poured onto an ice-cold solution of HCl 37% (340 mL) and water (560 mL). The crude product separated as a yellow solid, which was filtered and dissolved in dichloromethane. The solution was dried over Na$_2$SO$_4$, filtered and concentrated in vacuo. The crude product was purified on a silica eluting with a gradient formed from heptane and ethyl acetate. Evaporation of the product fractions yielded 6.9 g (51%) of the title compound as yellow solid.

b) step 2:

2-(5-Methyl-thiophen-2-yl)-ethylamine

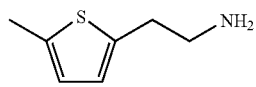

To a suspension of 6.9 g (40.78 mmol) LiAlH$_4$ in 70 mL diethyl ether under nitrogen was added drop wise a solution of 6.9 g (175 mmol) 2-methyl-5-((E)-2-nitro-vinyl)-thiophene in 150 mL diethyl ether at 20 to 25° C. After complete addition the mixture was heated to reflux for 5 h. The mixture was cooled to 0° C. and 28 mL water and 7 mL 5N NaOH and was added. The white solid was filtered, washed with ethyl acetate and the filtrate was concentrated in vacuo. The residue was distilled at reduced pressure to yield 4.98 g (86%) of the title compound as colourless liquid.

MS(m/e): 142.2 (MH$^+$).

c) step 3:

N-[2-(5-Methyl-thiophen-2-yl)-ethyl]-3-(4-trifluoromethyl-phenyl)-propionamide

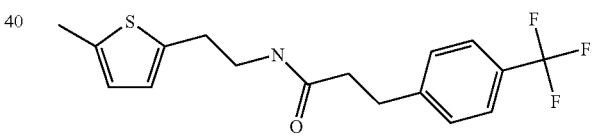

To a solution of 3 g (13 mmol) 4-(trifluoromethyl)hydrocinnamic acid (commercially available) in 30 mL DMF under argon were added 4.7 g (14.37 mmol) TBTU and 11.2 mL (65.3 mmol) N-ethyldiisopropylamine. A solution of 1.85 g (13 mmol) 2-(5-methyl-thiophen-2-yl)-ethylamine in 5 mL DMF was added drop wise over a period of 2 minutes. The mixture was stirred at room temperature for 1 h. The solvent was removed in vacuo and the residue was dissolved in ethyl acetate. The solution was washed with water and with a sat. NaHCO$_3$ solution, dried over Na$_2$SO$_4$, filtered and concentrated in vacuo. The solid was stirred in 30 mL ether, filtered and dried. The mother liquor was concentrated in vacuo and purified on silica eluting with a gradient formed from heptane and ethyl acetate. The product containing fractions were evaporated. 3.75 g (84%) of the title compound was yielded as white solid.

MS(m/e): 342.0 (MH$^+$).

d) step 4:

2-Methyl-4-[2-(4-trifluoromethyl-phenyl)-ethyl]-6,7-dihydro-thieno[3,2-c]pyridine

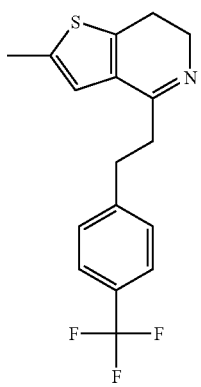

To a suspension of 762 mg (2.23 mmol) N-[2-(5-methyl-thiophen-2-yl)-ethyl]-3-(4-trifluoromethyl-phenyl)-propionamide in 10 mL acetonitrile was added 460 uL (4.91 mmol) POCl$_3$. The mixture was heated to reflux for 1 h and the solvent was removed in vacuo. The residue was taken up in toluene and concentrated again in vacuo. The oil was dissolved in dichloromethane and was basified with sat. NaHCO$_3$. The organic layer was dried over Na$_2$SO$_4$, filtered and concentrated in vacuo. 740 mg of the title compound was isolated which was used without further purification in the consecutive step.

MS(m/e): 324.2 (MH$^+$).

e) step 5:

2-Methyl-4-[2-(4-trifluoromethyl-phenyl)-ethyl]-4,5,6,7-tetrahydro-thieno[3,2-c]pyridine

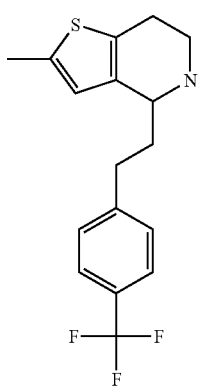

To a solution of 740 mg 2-methyl-4-[2-(4-trifluoromethyl-phenyl)-ethyl]-6,7-dihydro-thieno[3,2-c]pyridine in 7.4 mL methanol was added portion wise 82 mg (2.17 mmol) NaBH$_4$ at room temperature. The mixture was stirred at room temperature for 30 minutes, cooled in an ice bath and quenched with water and 1N HCl. The methanol was removed in vacuo and the residue stirred in water. The mixture was basified with a 2M Na$_2$CO$_3$ solution and extracted with dichloromethane. The combined organic extracts were dried over Na$_2$SO$_4$, filtered and concentrated in vacuo. The residue was purified on silica eluting with a gradient formed from heptane and ethyl acetate. The product containing fractions were evaporated to yield 630 mg (87%; over two steps) of the title compound as yellow oil. MS(m/e): 326.1 (MH$^+$).

f) step 6:

N-Methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and
N-Methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2)

To a solution of 300 mg (0.92 mmol) 2-methyl-4-[2-(4-trifluoromethyl-phenyl)-ethyl]-4,5,6,7-tetrahydro-thieno[3,2-c]pyridine in 13 mL acetonitrile was added 210.3 mg (0.92 mmol) 2-Bromo-N-methyl-2-phenyl-acetamide (commercially available), 473 uL (2.76 mmol) N-ethyldiisopropylamine and 138 mg (0.92 mmol) sodium iodide. The solution was stirred for 18 h at 60° C. The solvent was removed in vacuo and the residue was dissolved in ethyl acetate and washed with water and Na$_2$CO$_3$ aq. The organic layer was dried over Na$_2$SO$_4$, filtered and evaporated. The residue was purified on silica eluting with a gradient formed from heptane and ethyl acetate. The diastereoisomeric product eluting first (obtained after evaporation from the product containing fractions) was dissolved in methanol, treated with Norit, heated to reflux, filtered and evaporated to dryness to yield 46 mg (11%) of N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) (MS(m/e): 472.9 (MH$^+$)) as light yellow oil.

The diastereoisomeric product eluting second (obtained after evaporation from the product containing fractions) was again purified on silica eluting with a gradient formed from heptane and ethyl acetate. The product containing fractions were evaporated to yield 73 mg (17%) of the N-methyl-2-{2-methyl-4-[2-(4-trifluoromethyl-phenyl)-ethyl]-6,7-dihydro-4H-thieno [3,2-c]pyridin-5-yl}-2-phenyl-acetamide (diastereoisomer 2) (MS(m/e): 473.0 (MH$^+$)) as yellow oil.

EXAMPLE 5 AND EXAMPLE 6

N-Methyl-2-{2-methyl-4-[2-(4-trifluoromethyl-phenyl)-ethyl]-6,7-dihydro-4H-thieno[3,2-c]pyridin-5-yl}-2-phenyl-acetamide (enantiomer 1)

N-Methyl-2-{2-methyl-4-[2-(4-trifluoromethyl-phenyl)-ethyl]-6,7-dihydro-4H-thieno[3,2-c]pyridin-5-yl}-2-phenyl-acetamide (enantiomer 2)

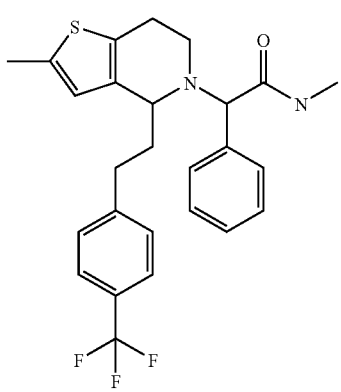

Example 5: enantiomer 1
Example 6: enantiomer 2

N-Methyl-2-{2-methyl-4-[2-(4-trifluoromethyl-phenyl)-ethyl]-6,7-dihydro-4H-thieno [3,2-c]pyridin-5-yl}-2-phenyl-acetamide (diastereoisomer 2) was subjected to column chromatography on chiral phase to yield N-methyl-2-{2-methyl-4-[2-(4-trifluoromethyl-phenyl)-ethyl]-6,7-dihydro-4H-thieno[3,2-c]pyridin-5-yl}-2-phenyl-acetamide (enantiomer 1, first eluting enantiomer)

MS(m/e): 472.9 (MH$^+$) as light yellow foam and N-methyl-2-{2-methyl-4-[2-(4-trifluoromethyl-phenyl)-ethyl]-6,7-dihydro-4H-thieno[3,2-c]pyridin-5-yl}-2-phenyl-acetamide (enantiomer 2, second eluting enantiomer)

MS(m/e): 472.9 (MH$^+$) as light yellow foam.

EXAMPLE 7

2-{4-[2-(4-Methoxy-phenyl)-ethyl]-2-methyl-6,7-dihydro-4H-thieno[3,2-c]pyridin-5-yl}-N-methyl -2-phenyl-acetamide (diastereoisomer 2)

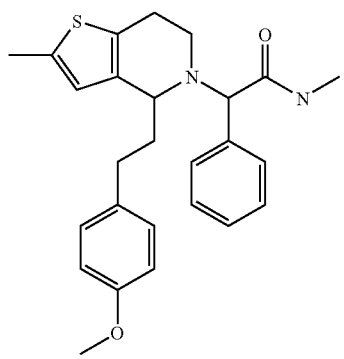

a) step 1:

3-(4-Methoxy-phenyl)-N-[2-(5-methyl-thiophen-2-yl)-ethyl]-propionamide

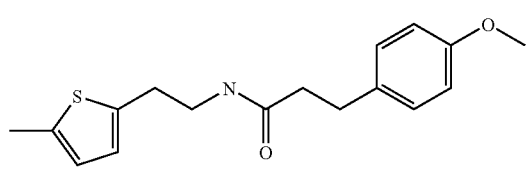

In analogy to the procedure described for the synthesis of N-[2-(5-methyl-thiophen-2-yl)-ethyl]-3-(4-trifluoromethyl-phenyl)-propionamide (example 3/4; step 3) the title compound was prepared from 3-(4-Methoxyphenyl)propionic acid (commercially available) and 2-(5-methyl-thiophen-2-yl)-ethylamine as yellow solid.

MS(m/e): 304.0 (MH$^+$)

b) step 2:

4-[2-(4-Methoxy-phenyl)-ethyl]-2-methyl-6,7-dihydro-thieno[3,2-c]pyridine

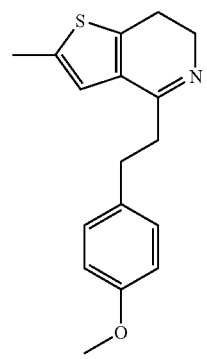

In analogy to the procedure described for the synthesis of 2-methyl-4-[2-(4-trifluoromethyl-phenyl)-ethyl]-6,7-dihydro-thieno[3,2-c]pyridine (example 3/4; step 4) the title compound was prepared from 3-(4-methoxy-phenyl)-N-[2-(5-methyl-thiophen-2-yl)-ethyl]-propionamide.

MS(m/e): 286.0 (MH$^+$).

c) step 3:

4-[2-(4-Methoxy-phenyl)-ethyl]-2-methyl-4,5,6,7-tetrahydro-thieno[3,2-c]pyridine

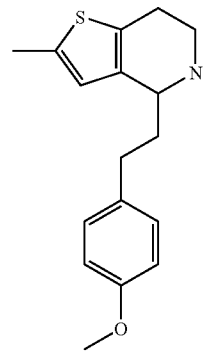

In analogy to the procedure described for the synthesis of 2-methyl-4-[2-(4-trifluoromethyl-phenyl)-ethyl]-4,5,6,7-tetrahydro-thieno[3,2-c]pyridine (example 3/4; step 5) the title compound was prepared from 4-[2-(4-methoxy-phenyl)-ethyl]-2-methyl-6,7-dihydro-thieno [3,2-c]pyridine as yellow oil.

MS(m/e): 288.0 (MH$^+$).

d) step 4:

2-{4-[2-(4-Methoxy-phenyl)-ethyl]-2-methyl-6,7-dihydro-4H-thieno[3,2-c]pyridin-5-yl}-N-methyl -2-phenyl-acetamide (diastereoisomer 2)

In analogy to the procedure described for the synthesis of example 3N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and example 4N-methyl-2-{2-methyl-4-[2-(4-trifluoromethyl-phenyl)- ethyl]-6,7-dihydro-4H-thieno[3,2-c]pyridin-5-yl}-2-phenyl-acetamide (diastereoisomer 2) the title compound was prepared from 2-bromo-N-methyl-2-phenyl-acetamide (commercially available) and 4-[2-(4-methoxy-phenyl)-ethyl]-2-methyl-4,5,6,7-tetrahydro-thieno[3,2-c]pyridine as yellow-brown foam (second eluting diastereoisomer on silica using a gradient formed from heptane and ethyl acetate MS(m/e): 435.0 (MH+).

EXAMPLE 8 AND EXAMPLE 9

2-{4-[2-(4-Methoxy-phenyl)-ethyl]-2-methyl-6,7-dihydro-4H-thieno[3,2-c]pyridin-5-yl}-N-methyl -2-phenyl-acetamide (enantiomer 1)

2-{4-[2-(4-Methoxy-phenyl)-ethyl]-2-methyl-6,7-dihydro-4H-thieno[3,2-c]pyridin-5-yl}-N-methyl -2-phenyl-acetamide (enantiomer 2)

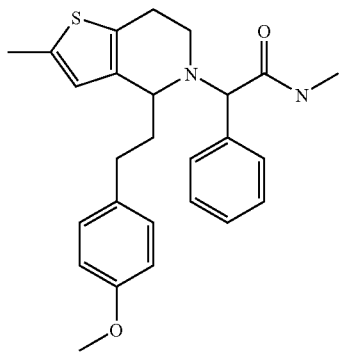

Example 8: enantiomer 1

Example 9: enantiomer 2

2-{4-[2-(4-Methoxy-phenyl)-ethyl]-2-methyl-6,7-dihydro-4H-thieno[3,2-c]pyridin-5-yl}-N-methyl-2-phenyl-acetamide (diastereoisomer 2) was subjected to column chromatography on chiral phase to yield 2-{4-[2-(4-methoxy-phenyl)-ethyl]-2-methyl-6,7-dihydro-4H-thieno [3,2-c] pyridin-5-yl}-N-methyl-2-phenyl-acetamide (enantiomer 1, first eluting enantiomer) (MS(m/e): 435.2 (MH+)) as yellow foam and 2-{4-[2-(4-methoxy-phenyl)-ethyl]-2-methyl-6,7-dihydro-4H-thieno[3,2-c]pyridin-5-yl}-N-methyl-2-phenyl-acetamide (enantiomer 2, second eluting enantiomer)

(MS(m/e): 435.2 (MH+)) as yellow foam.

EXAMPLE 10 AND EXAMPLE 11

2-{5-[2-(4-Methoxy-phenyl)-ethyl]-7,8-dihydro-5H-[1,6]naphthyridin-6-yl}-N-methyl-2-phenyl-acetamide (diastereoisomer 1)

2-{5-[2-(4-Methoxy-phenyl)-ethyl]-7,8-dihydro-5H-[1,6]naphthyridin-6-yl}-N-methyl-2-phenyl-acetamide (diastereoisomer 2)

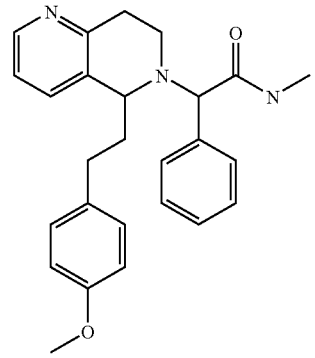

Example 10: diastereoisomer 1
Example 11: diastereoisomer 2
a) step 1:

6-Benzyl-5-[2-(4-methoxy-phenyl)-ethyl]-5,6-dihydro-[1,6]naphthyridine

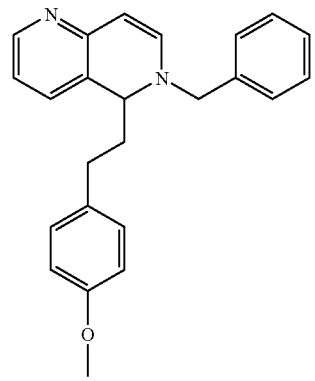

To a suspension of 581 mg (23.9 mmol) magnesium in 24 mL THF was added 5.3 g (23.9 mmol) 4-methoxyphenethyl bromide. The mixture was refluxed for 2 h and then cooled in an ice bath and 2.4 g (7.97 mmol) 6-benzyl-[1,6]naphthyridin-6-ium bromide (Chemical & Pharmaceutical Bulletin, 32(7), 2522-9; 1984) was added at once. The mixture was stirred at room temperature for 30 minutes, cooled to 0° C. and quenched with a 20% NH4Cl solution. The mixture was extracted with ethyl acetate. The combined extracts were dried over Na2SO4, filtered and concentrated in vacuo. The residue was purified on silica eluting with a gradient formed from heptane and ethyl acetate. The product containing fractions were evaporated to yield 2.57 g (90%) of the title compound was yielded as yellow oil.

MS(m/e): 357.3 (MH+).

b) step 2:

5-[2-(4-Methoxy-phenyl)-ethyl]-5,6,7,8-tetrahydro-[1,6]naphthyridine

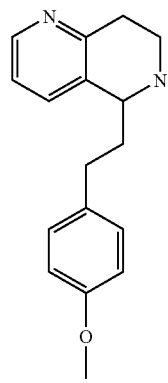

To a solution of 2.1 g (5.85 mmol) 6-benzyl-5-[2-(4-methoxy-phenyl)-ethyl]-5,6-dihydro-[1,6]naphthyridine in 70 mL methanol and 7 mL acetic acid was added 210 mg Pd/C 10% and hydrogenated at atmospheric pressure for 4 h at 55° C. The apparatus was purged with argon, the catalyst was filtered and the filtrate was concentrated in vacuo. The oil was dissolved in ethyl acetate and the solution was washed once with a sat. NaHCO$_3$ solution. The aqueous layer was extracted twice with ethyl acetate and the combined organic layers were dried over Na$_2$SO$_4$, filtered and concentrated in vacuo to yield 1.47 g (93%) of the title compound was yielded as yellow oil.

MS(m/e): 269.2 (MH$^+$).

c) step 3:

To a solution of 615 mg (2.29 mmol) 5-[2-(4-methoxy-phenyl)-ethyl]-5,6,7,8-tetrahydro-[1,6]naphthyridine in 25 mL acetonitrile, were added 682 mg (2.98 mmol) 2-bromo-N-methyl -2-phenyl-acetamide, 1.2 mL (6.87 mmol) N-ethyldiisopropylamine and 343 mg (2.29 mmol) sodium iodide. The solution was stirred at 60° C. for 6 h. The solvent was removed in vacuo and the residue was taken in ethyl acetate. The mixture was washed once with water and once with a 2M Na$_2$CO$_3$ solution, dried over Na$_2$SO$_4$, filtered and concentrated in vacuo. The residue was purified on silica eluting with a gradient formed from heptane and ethyl acetate. The product containing fractions were evaporated to yield 330 mg (35%) of 2-{5-[2-(4-methoxy-phenyl)-ethyl]-7,8-dihydro-5H-[1,6]naphthyridin-6-yl}-N-methyl-2-phenyl-acetamide (diastereoisomer 1, first eluting diastereoisomer) as yellow foam (MS(m/e): 416.4 MH$^+$)).

The other crude diastereoisomeric product (obtained after evaporation from the product containing fractions) was taken up in methanol, Norit was added, heated to reflux, cooled to room temperature, filtered and evaporated to yield 280 mg (29%) of 2-{5-[2-(4-Methoxy-phenyl)-ethyl]-7,8-dihydro-5H-[1,6]naphthyridin-6-yl}-N-methyl-2-phenyl-acetamide (diastereoisomer 2, second eluting diastereoisomer) as light brown foam (MS(m/e): 416.4 MH$^+$)).

EXAMPLE 12 AND EXAMPLE 13

2-{4-[2-(4-Methoxy-phenyl)-ethyl]-2,3-dimethyl-6,7-dihydro-4H-thieno[3,2-c]pyridin-5-yl}-N-methyl -2-phenyl-acetamide (diastereoisomer 1)

2-{4-[2-(4-Methoxy-phenyl)-ethyl]-2,3-dimethyl-6,7-dihydro-4H-thieno[3,2-c]pyridin-5-yl}-N-methyl -2-phenyl-acetamide (diastereoisomer 2)

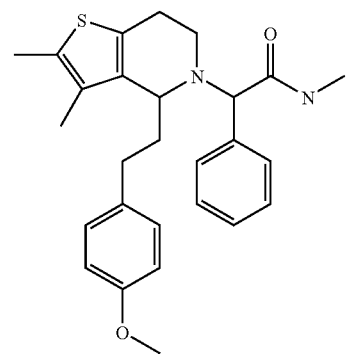

Example 12: diastereoisomer 1
Example 13: diastereoisomer 2 a) step 1:

N-[2-(4,5-Dimethyl-thiophen-2-yl)-ethyl]-3-(4-methoxy-phenyl)-propionamide

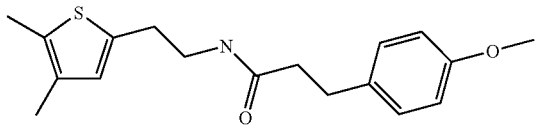

In analogy to the procedure described for the synthesis of N-[2-(5-methyl-thiophen-2-yl)-ethyl]-3-(4-trifluoromethyl-phenyl)-propionamide (example 3/4; step 3) the title compound was prepared from 3-(4-methoxyphenyl)propionic acid (commercially available) and 2-(4,5-dimethyl-thiophen-2-yl)-ethylamine (commercially available) as yellow solid. MS(m/e): 318.0 (MH$^+$).

b) step 2:

4-[2-(4-Methoxy-phenyl)-ethyl]-2,3-dimethyl-6,7-dihydro-thieno[3,2-c]pyridine

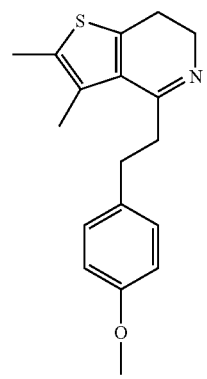

In analogy to the procedure described for the synthesis of 2-methyl-4-[2-(4-trifluoromethyl-phenyl)-ethyl]-6,7-dihydro-thieno[3,2-c]pyridine (example 3/4; step 4) the title compound was prepared from N-[2-(4,5-dimethyl-thiophen-2-yl)-ethyl]-3-(4-methoxy-phenyl)-propionamide as yellow oil. MS(m/e): 300.1 (MH+).

c) step 3:

4-[2-(4-Methoxy-phenyl)-ethyl]-2,3-dimethyl-4,5,6,7-tetrahydro-thieno[3,2-c]pyridine

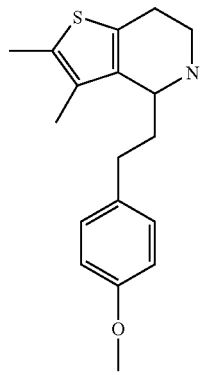

In analogy to the procedure described for the synthesis of 2-methyl-4-[2-(4-trifluoromethyl-phenyl)-ethyl]-4,5,6,7-tetrahydro-thieno[3,2-c]pyridine (example 3/4; step 5) the title compound was prepared from 4-[2-(4-methoxy-phenyl)-ethyl]-2,3-dimethyl-6,7-dihydro-thieno[3,2-c]pyridine as yellow oil. MS(m/e): 302.2 (MH+).

d) step 4:

2-{4-[2-(4-Methoxy-phenyl)-ethyl]-2,3-dimethyl-6,7-dihydro-4H-thieno[3,2-c]pyridin-5-yl}-N-methyl -2-phenyl-acetamide (diastereoisomer 1)

2-{4-[2-(4-Methoxy-phenyl)-ethyl]-2,3-dimethyl-6,7-dihydro-4H-thieno[3,2-c]pyridin-5-yl}-N-methyl -2-phenyl-acetamide (diastereoisomer 2)

In analogy to the procedure described for the synthesis of example 3N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and example 4N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2) the title compounds, 2-{4-[2-(4-methoxy-phenyl)-ethyl]-2,3-dimethyl-6,7-dihydro-4H-thieno[3,2-c]pyridin-5-yl}-N-methyl-2-phenyl-acetamide (diastereoisomer 1, first eluting diastereoisomer on silica using a gradient formed from heptane and ethyl acetate) (MS(m/e): 449.2 (MH+)) and 2-{4-[2-(4-methoxy-phenyl)-ethyl]-2,3-dimethyl-6,7-dihydro-4H-thieno [3,2-c]pyridin-5-yl}-N-methyl-2-phenyl-acetamide (diastereoisomer 2, second eluting diastereoisomer on silica using a gradient formed from heptane and ethyl acetate) (MS(m/e): 449.1 (MH+)), were prepared from 2-bromo-N-methyl-2-phenyl-acetamide (commercially available) and 4-[2-(4-methoxy-phenyl)-ethyl]-2,3-dimethyl-4,5,6,7-tetrahydro-thieno [3,2-c]pyridine both as light brown solid.

EXAMPLE 14 AND EXAMPLE 15

2-{4-[2-(4-Methoxy-phenyl)-ethyl]-2,3-dimethyl-6,7-dihydro-4H-thieno[3,2-c]pyridin-5-yl}-N-methyl -2-phenyl-acetamide (enantiomer 1)

2-{4-[2-(4-Methoxy-phenyl)-ethyl]-2,3-dimethyl-6,7-dihydro-4H-thieno[3,2-c]pyridin-5-yl}-N-methyl -2-phenyl-acetamide (enantiomer 2)

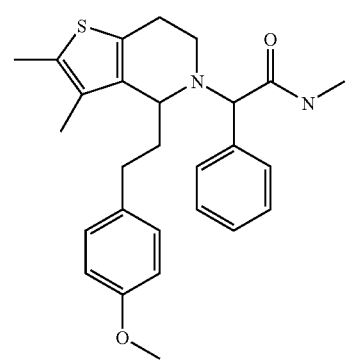

Example 14: enantiomer 1
Example 15: enantiomer 2

2-{4-[2-(4-Methoxy-phenyl)-ethyl]-2,3-dimethyl-6,7-dihydro-4H-thieno[3,2-c]pyridin -5-yl}-N-methyl-2-phenyl-acetamide (diastereoisomer 2) was subjected to column chromatography on chiral phase to yield 2-{4-[2-(4-methoxyphenyl)-ethyl]-2,3-dimethyl-6,7-dihydro-4H-thieno[3,2-c]pyridin-5-yl}-N-methyl-2-phenyl-acetamide (enantiomer 1, first eluting enantiomer) (MS(m/e): 449.1 (MH+)) as white foam and 2-{4-[2-(4-methoxy-phenyl)-ethyl]-2,3-dimethyl-6,7-dihydro-4H-thieno[3,2-c]pyridin-5-yl}-N-methyl-2-phenyl-acetamide (enantiomer 2, second eluting enantiomer) (MS(m/e): 449.1 (MH+)) as white foam.

EXAMPLE 16

N-Methyl-2-phenyl-2-{7-[2-(4-trifluoromethyl-phenyl)-ethyl]-4,7-dihydro-5H-thieno[2,3-c]pyridin-6-yl}-acetamide (diastereoisomer 2)

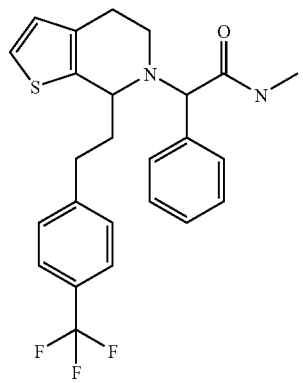

a) step 1:

N-(2-Thiophen-3-yl-ethyl)-3-(4-trifluoromethyl-phenyl)-propionamide

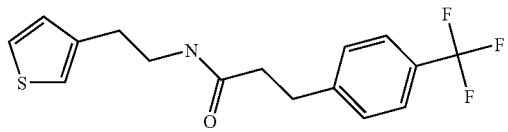

In analogy to the procedure described for the synthesis of N-[2-(5-methyl-thiophen-2-yl)-ethyl]-3-(4-trifluoromethyl-phenyl)-propionamide (example 3/4; step 3) the title compound was prepared from 3-(4-trifluoromethyl-phenyl)-propionic acid (commercially available) and 2-thiophen-3-yl-ethylamine (commercially available) as off-white solid.
MS(m/e): 327.1 (MH$^+$).

b) step 2:

7-[2-(4-Trifluoromethyl-phenyl)-ethyl]-4,5-dihydro-thieno[2,3-c]pyridine

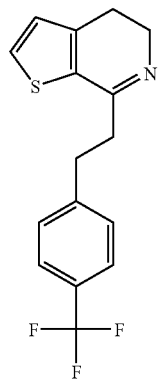

In analogy to the procedure described for the synthesis of 2-methyl-4-[2-(4-trifluoromethyl-phenyl)-ethyl]-6,7-dihydro-thieno[3,2-c]pyridine (example 3/4; step 4) the title compound was prepared from N-(2-thiophen-3-yl-ethyl)-3-(4-trifluoromethyl-phenyl)-propionamide as light red oil.
MS(m/e): 309.9 (MH$^+$).

c) step 3:

7-[2-(4-Trifluoromethyl-phenyl)-ethyl]-4,5,6,7-tetrahydro-thieno[2,3-c]pyridine

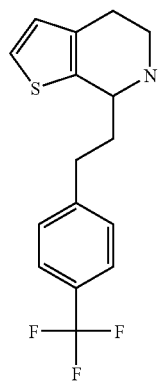

In analogy to the procedure described for the synthesis of 2-methyl-4-[2-(4-trifluoromethyl-phenyl)-ethyl]-4,5,6,7-tetrahydro-thieno[3,2-c]pyridine (example 3/4; step 5) the title compound was prepared from 7-[2-(4-trifluoromethyl-phenyl)-ethyl]-4,5-dihydro-thieno [2,3-c]pyridine as yellow oil.
MS(m/e): 311.9 (MH$^+$).

d) step 4:

N-Methyl-2-phenyl-2-{7-[2-(4-trifluoromethyl-phenyl)-ethyl]-4,7-dihydro-5H-thieno[2,3-c]pyridin-6-yl}-acetamide (diastereoisomer 2)

In analogy to the procedure described for the synthesis of example 3N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and example 4N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2) the title compound, N-methyl-2-phenyl-2-{7-[2-(4-trifluoromethyl-phenyl)-ethyl]-4,7-dihydro-5H-thieno[2,3-c]pyridin-6-yl}-acetamide (diastereoisomer 2), was prepared from 2-bromo-N-methyl-2-phenyl-acetamide (commercially available) and 7-[2-(4-trifluoromethyl-phenyl)-ethyl]-4,5,6,7-tetrahydro-thieno[2,3-c]pyridine (second eluting diastereoisomer on silica using a gradient formed from heptane and ethyl acetate.
MS(m/e): 459.2 (MH$^+$).

EXAMPLE 17

2-{2-Chloro-4-[2-(4-methoxy-phenyl)-ethyl]-6,7-dihydro-4H-thieno[3,2-c]pyridin-5-yl}-N-methyl-2-phenyl-acetamide (diastereoisomer 2)

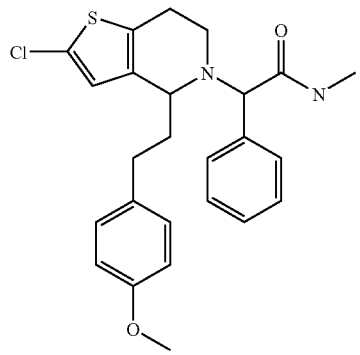

a) step 1:

N-[2-(5-Chloro-thiophen-2-yl)-ethyl]-3-(4-methoxy-phenyl)-propionamide

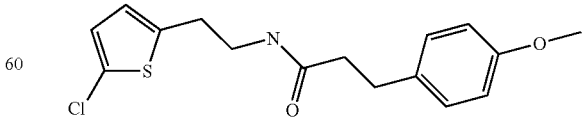

In analogy to the procedure described for the synthesis of N-[2-(5-methyl-thiophen-2-yl)-ethyl]-3-(4-trifluoromethyl-phenyl)-propionamide (example 3/4; step 3) the title compound was prepared from 3-(4-methoxyl-phenyl)-propionic acid (commercially available) and 2-(5-chloro-thiophen-2-yl)-ethylamine (commercially available) as light brown solid.
MS(m/e): 324.2 (MH⁺).
b) step 2:

2-Chloro-4-[2-(4-methoxy-phenyl)-ethyl]-6,7-dihydro-thieno[3,2-c]pyridine

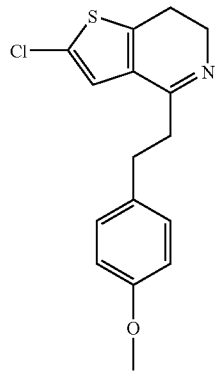

In analogy to the procedure described for the synthesis of 2-methyl-4-[2-(4-trifluoromethyl-phenyl)-ethyl]-6,7-dihydro-thieno[3,2-c]pyridine (example 3/4; step 4) the title compound was prepared from N-[2-(5-chloro-thiophen-2-yl)-ethyl]-3-(4-methoxy-phenyl)-propionamide as brown oil.
MS(m/e): 306.2 (MH⁺).
c) step 3:

2-Chloro-4-[2-(4-methoxy-phenyl)-ethyl]-4,5,6,7-tetrahydro-thieno[3,2-c]pyridine

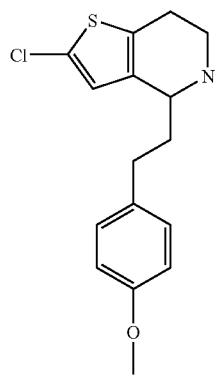

In analogy to the procedure described for the synthesis of 2-methyl-4-[2-(4-trifluoromethyl-phenyl)-ethyl]-4,5,6,7-tetrahydro-thieno[3,2-c]pyridine (example 3/4; step 5) the title compound was prepared from 2-chloro-4-[2-(4-methoxy-phenyl)-ethyl]-6,7-dihydro-thieno [3,2-c]pyridine as yellow oil.
MS(m/e): 308.2 (MH⁺).
d) step 4:

2-{2-Chloro-4-[2-(4-methoxy-phenyl)-ethyl]-6,7-dihydro-4H-thieno[3,2-c]pyridin-5-yl}-N-methyl -2-phenyl-acetamide (diastereoisomer 2)

In analogy to the procedure described for the synthesis of example 3N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and example 4N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2) the title compound, 2-{2-Chloro-4-[2-(4-methoxy-phenyl)-ethyl]-6,7-dihydro-4H-thieno[3,2-c]pyridin-5-yl}-N-methyl-2-phenyl-acetamide (diastereoisomer 2), was prepared from 2-bromo-N-methyl-2-phenyl-acetamide (commercially available) and 2-chloro-4-[2-(4-methoxy-phenyl)-ethyl]-4,5,6,7-tetrahydro-thieno[3,2-c]pyridine as light brown oil (second eluting diastereoisomer on silica using a gradient formed from heptane and ethyl acetate).
MS(m/e): 455.2 (MH⁺).

EXAMPLE 18 AND EXAMPLE 19

2-{2-Chloro-4-[2-(4-methoxy-phenyl)-ethyl]-6,7-dihydro-4H-thieno[3,2-c]pyridin-5-yl}-N-methyl -2-phenyl-acetamide (enantiomer 1)

2-{2-Chloro-4-[2-(4-methoxy-phenyl)-ethyl]-6,7-dihydro-4H-thieno[3,2-c]pyridin-5-yl}-N-methyl -2-phenyl-acetamide (enantiomer 2)

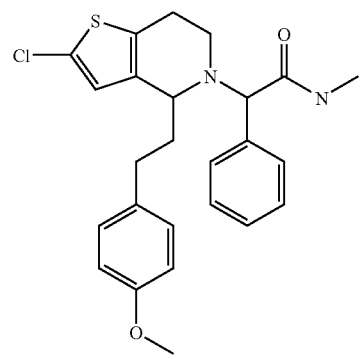

Example 18: enantiomer 1

Example 19: enantiomer 2

2-{2-Chloro-4-[2-(4-methoxy-phenyl)-ethyl]-6,7-dihydro-4H-thieno[3,2-c]pyridin-5-yl}-N-methyl-2-phenyl-acetamide (diastereoisomer 2) was subjected to column chromatography on chiral phase to yield 2-{2-chloro-4-[2-(4-methoxy-phenyl)-ethyl]-6,7-dihydro-4H-thieno [3,2-c]pyridin-5-yl}-N-methyl-2-phenyl-acetamide (enantiomer 1, first eluting enantiomer) (MS(m/e): 455.1 (MH⁺)) as white foam and 2-{2-chloro-4-[2-(4-methoxy-phenyl)-ethyl]-6,7-dihydro-4H-thieno[3,2-c]pyridin-5-yl}-N-methyl-2-phenyl-acetamide (enantiomer 2, second eluting enantiomer) (MS(m/e): 455.2 (MH⁺)) as white foam.

EXAMPLE 20

2-{3-Chloro-4-[2-(4-methoxy-phenyl)-ethyl]-6,7-dihydro-4H-thieno[3,2-c]pyridin-5-yl}-N-methyl-2-phenyl-acetamide (diastereoisomer 2)

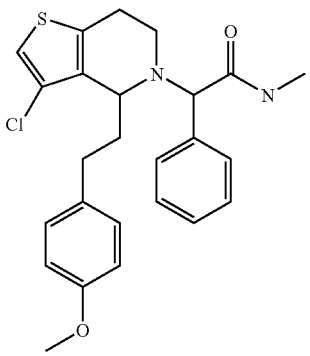

a) step 1:

4-Chloro-2-((E)-2-nitro-vinyl)-thiophene

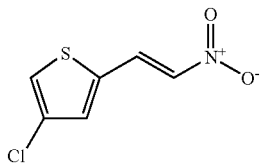

In analogy to the procedure described for the synthesis of 2-methyl-5-((E)-2-nitro-vinyl)-thiophene (example 3/4, step 1) the title compound was prepared from 4-chloro-thiophene-2-carbaldehyde (Journal of Heterocyclic Chemistry (1976), 13(2), 393-4) and nitromethane as yellow powder.

b) step 2:

2-(4-Chloro-thiophen-2-yl)-ethylamine

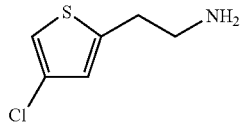

In analogy to the procedure described for the synthesis of 2-(5-methyl-thiophen-2-yl)-ethylamine (example 3/4, step 2) the title compound was prepared from 4-chloro-2-((E)-2-nitro-vinyl)-thiophene as colourless liquid. bp: 90° C., 2.1 mbar.

c) step 3:

N-[2-(4-Chloro-thiophen-2-yl)-ethyl]-3-(4-methoxy-phenyl)-propionamide

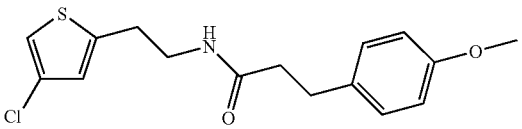

In analogy to the procedure described for the synthesis of N-[2-(5-methyl-thiophen-2-yl)-ethyl]-3-(4-trifluoromethyl-phenyl)-propionamide (example 3/4; step 3) the title compound was prepared from 3-(4-methoxyphenyl)propionic acid (commercially available) and 2-(4-chloro-thiophen-2-yl)-ethylamine as white solid.

MS(m/e): 324.2 (MH$^+$).

d) step 4:

3-Chloro-4-[2-(4-methoxy-phenyl)-ethyl]-6,7-dihydro-thieno[3,2-c]pyridine

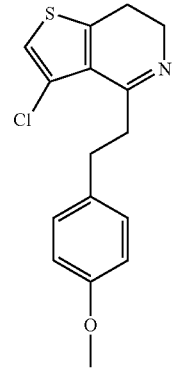

In analogy to the procedure described for the synthesis of 2-methyl-4-[2-(4-trifluoromethyl-phenyl)-ethyl]-6,7-dihydro-thieno[3,2-c]pyridine (example 3/4; step 4) the title compound was prepared from N-[2-(4-chloro-thiophen-2-yl)-ethyl]-3-(4-methoxy-phenyl)-propionamide.

MS(m/e): 306.1 (MH$^+$).

e) step 5:

3-Chloro-4-[2-(4-methoxy-phenyl)-ethyl]-4,5,6,7-tetrahydro-thieno[3,2-c]pyridine

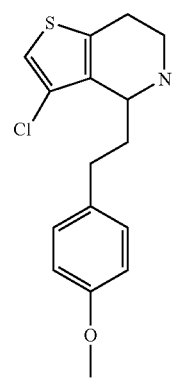

In analogy to the procedure described for the synthesis of 2-methyl-4-[2-(4-trifluoromethyl-phenyl)-ethyl]-4,5,6,7-tetrahydro-thieno[3,2-c]pyridine (example 3/4; step 5) the title compound was prepared from 3-chloro-4-[2-(4-methoxy-phenyl)-ethyl]-6,7-dihydro-thieno [3,2-c]pyridine as yellow oil.

MS(m/e): 308.2 (MH⁺).

f) step 6:

2-{3-Chloro-4-[2-(4-methoxy-phenyl)-ethyl]-6,7-dihydro-4H-thieno[3,2-c]pyridin-5-yl}-N-methyl -2-phenyl-acetamide (diastereoisomer 2)

In analogy to the procedure described for the synthesis of example 3N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 1) and example 4N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2) the title compound, 2-{3-chloro-4-[2-(4-methoxy-phenyl)-ethyl]-6,7-dihydro-4H-thieno[3,2-c]pyridin-5-yl}-N-methyl-2-phenyl-acetamide (diastereoisomer 2), was prepared from 2-bromo-N-methyl-2-phenyl-acetamide (commercially available) and 3-chloro-4-[2-(4-methoxy-phenyl)-ethyl]-4,5,6,7-tetrahydro-thieno[3,2-c]pyridine as orange foam (second eluting diastereoisomer on silica using a gradient formed from heptane and ethyl acetate).

MS(m/e): 455.2 (MH⁺).

EXAMPLE 21 AND EXAMPLE 22

2-{5-[2-(4-Methoxy-phenyl)-ethyl]-7,8-dihydro-5H-[1,6]naphthyridin-6-yl}-N-methyl-2-phenyl-acetamide (enantiomer 1)

2-{5-[2-(4-Methoxy-phenyl)-ethyl]-7,8-dihydro-5H-[1,6]naphthyridin-6-yl}-N-methyl-2-phenyl-acetamide (enantiomer 2)

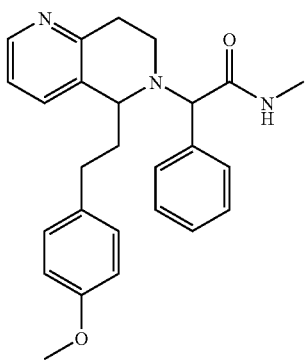

Example 21: enantiomer 1
Example 22: enantiomer 2

2-{5-[2-(4-Methoxy-phenyl)-ethyl]-7,8-dihydro-5H-[1,6]naphthyridin-6-yl}-N-methyl -2-phenyl-acetamide (diastereoisomer 2, example 11) was subjected to column chromatography on chiral phase to yield 2-{5-[2-(4-methoxy-phenyl)-ethyl]-7,8-dihydro-5H-[1,6]naphthyridin -6-yl}-N-methyl-2-phenyl-acetamide (enantiomer 1, first eluting enantiomer) (MS(m/e): 416.3 (MH⁺)) as white foam and 2-{5-[2-(4-methoxy-phenyl)-ethyl]-7,8-dihydro-5H-[1,6]naphthyridin-6-yl}-N-methyl-2-phenyl-acetamide (enantiomer 2, second eluting enantiomer) (MS(m/e): 416.3 (MH⁺)) as white foam.

EXAMPLE 23

2-{5-[2-(3-Methoxy-phenyl)-ethyl]-7,8-dihydro-5H-[1,6]naphthyridin-6-yl}-N-methyl-2-phenyl-acetamide (diastereoisomer 2)

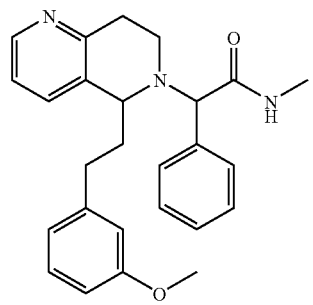

In analogy to the procedure described for the synthesis of 2-{5-[2-(4-Methoxy-phenyl)-ethyl]-7,8-dihydro-5H-[1,6]naphthyridin-6-yl}-N-methyl-2-phenyl-acetamide (diastereoisomer 2, example 11) the title compound was prepared from 6-benzyl-[1,6]naphthyridin-6-ium bromide (Chemical & Pharmaceutical Bulletin, 32(7), 2522-9; 1984 and 3-methoxyphenethyl bromide as white solid. MS(m/e): 416.1 (MH⁺).

EXAMPLE 24 AND EXAMPLE 25

2-{5-[2-(3-Methoxy-phenyl)-ethyl]-7,8-dihydro-5H-[1,6]naphthyridin-6-yl}-N-methyl-2-phenyl-acetamide (enantiomer 1)

2-{5-[2-(3-Methoxy-phenyl)-ethyl]-7,8-dihydro-5H-[1,6]naphthyridin-6-yl}-N-methyl-2-phenyl-acetamide (enantiomer 2)

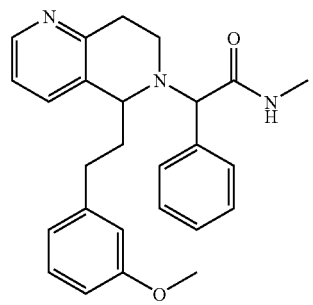

Example 24: enantiomer 1
Example 25: enantiomer 2

2-{5-[2-(3-Methoxy-phenyl)-ethyl]-7,8-dihydro-5H-[1,6]naphthyridin-6-yl}-N-methyl -2-phenyl-acetamide (diastereoisomer 2, example 23) was subjected to column chromatography on chiral phase to yield 2-{5-[2-(3-methoxy-phenyl)-ethyl]-7,8-dihydro-5H-[1,6]naphthyridin -6-yl}-N-methyl-2-phenyl-acetamide (enantiomer 1, first eluting enantiomer) (MS(m/e): 416.3 (MH⁺)) as white foam and 2-{5-[2-(3-methoxy-phenyl)-ethyl]-7,8-dihydro-5H -[1,6]

naphthyridin-6-yl}-N-methyl-2-phenyl-acetamide (enantiomer 2, second eluting enantiomer)
(MS(m/e): 416.3 (MH⁺)) as white foam.

EXAMPLE 26

N-Methyl-2-phenyl-2-{5-[2-(4-trifluoromethyl-phenyl)-ethyl]-7,8-dihydro-5H-[1,6]naphthyridin-6-yl}-acetamide (diastereoisomer 2)

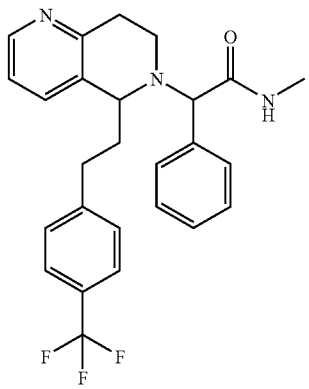

In analogy to the procedure described for the synthesis of 2-{5-[2-(4-methoxy-phenyl)-ethyl]-7,8-dihydro-5H-[1,6]naphthyridin-6-yl}-N-methyl-2-phenyl-acetamide (diastereoisomer 2, example 11) the title compound was prepared from 6-benzyl-[1,6]naphthyridin-6-ium bromide (Chemical & Pharmaceutical Bulletin, 32(7), 2522-9; 1984 and 4-trifluoromethylphenethyl bromide as white solid. MS(m/e): 454.2 (MH⁺).

EXAMPLE 27

2-{5-[2-(4-Fluoro-phenyl)-ethyl]-7,8-dihydro-5H-[1,6]naphthyridin-6-yl}-N-methyl-2-phenyl-acetamide (diastereoisomer 2)

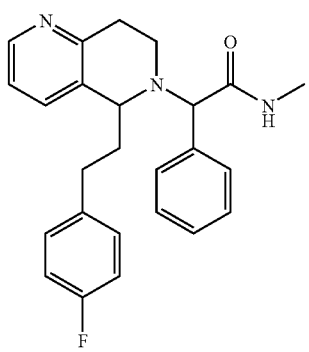

In analogy to the procedure described for the synthesis of 2-{5-[2-(4-methoxy-phenyl)-ethyl]-7,8-dihydro-5H-[1,6]naphthyridin-6-yl}-N-methyl-2-phenyl-acetamide (diastereoisomer 2, example 11) the title compound was prepared from 6-benzyl-[1,6]naphthyridin-6-ium bromide (Chemical & Pharmaceutical Bulletin, 32(7), 2522-9; 1984 and 4-fluoromethylphenethyl bromide as white solid. MS(m/e): 404.5 (MH⁺).

EXAMPLE 28

2-{5-[2-(4-Fluoro-phenyl)-ethyl]-7,8-dihydro-5H-[1,6]naphthyridin-6-yl}-N-methyl-2-phenyl-acetamide (enantiomer 2)

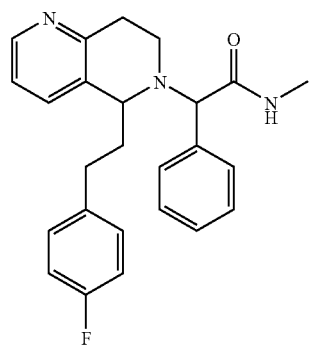

Example 28: enantiomer 2

2-{5-[2-(4-Fluoro-phenyl)-ethyl]-7,8-dihydro-5H-[1,6]naphthyridin-6-yl}-N-methyl-2-phenyl-acetamide (diastereoisomer 2, example 27) was subjected to column chromatography on chiral phase to yield 2-{5-[2-(4-Fluoro-phenyl)-ethyl]-7,8-dihydro-5H-[1,6]naphthyridin-6-yl}-N-methyl-2-phenyl-acetamide (enantiomer 2, second eluting enantiomer) (MS(m/e): 404.4 (MH⁺)) as white foam.

The invention claimed is:

1. A compound of formula I

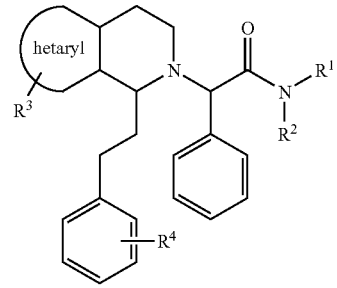

wherein
$R^1$ and $R^2$ are each independently hydrogen or lower alkyl;
$R^3$ is hydrogen, halogen, lower alkyl, lower alkyl substituted by halogen, lower alkoxy or lower alkoxy substituted by halogen;
$R^4$ is halogen, lower alkyl, lower alkyl substituted by halogen, lower alkoxy or lower alkoxy substituted by halogen;

hetaryl is a one or two ring-membered heteroaromatic ring system, connected to the carbon atoms of the piperidine group selected from the group consisting of

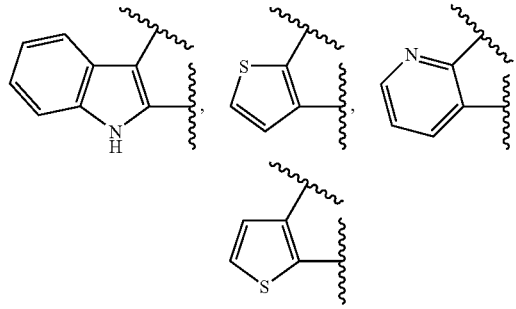

or a pharmaceutically suitable acid addition salt, enantiomer, racemate or diastereomeric mixture thereof.

2. A compound of claim 1, wherein one of $R^1$ or $R^2$ is hydrogen and the other is lower alkyl.

3. A compound of claim 2, wherein hetaryl is

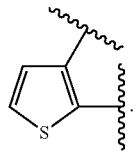

4. A compound of claim 3, selected from the group consisting of
N-methyl-2-{2-methyl-4-[2-(4-trifluoromethyl-phenyl)-ethyl]-6,7-dihydro-4H-thieno[3,2-c]pyridin-5-yl}-2-phenyl-acetamide (diastereoisomer 2);
N-methyl-2-{2-methyl-4-[2-(4-trifluoromethyl-phenyl)-ethyl]-6,7-dihydro-4H-thieno[3,2-c]pyridin-5-yl}-2-phenyl-acetamide (enantiomer 2);
2-{4-[2-(4-methoxy-phenyl)-ethyl]-2-methyl-6,7-dihydro-4H-thieno[3,2-c]pyridin-5-yl}-N-methyl -2-phenyl-acetamide (diastereoisomer 2);
2-{4-[2-(4-methoxy-phenyl)-ethyl]-2-methyl-6,7-dihydro-4H-thieno[3,2-c]pyridin-5-yl}-N-methyl -2-phenyl-acetamide (enantiomer 1);
2-{4-[2-(4-methoxy-phenyl)-ethyl]-2-methyl-6,7-dihydro-4H-thieno[3,2-c]pyridin-5-yl}-N-methyl -2-phenyl-acetamide (enantiomer 2);
2-{4-[2-(4-methoxy-phenyl)-ethyl]-2,3-dimethyl-6,7-dihydro-4H-thieno[3,2-c]pyridin-5-yl}-N-methyl-2-phenyl-acetamide (diastereoisomer 2);
2-{4-[2-(4-methoxy-phenyl)-ethyl]-2,3-dimethyl-6,7-dihydro-4H-thieno[3,2-c]pyridin-5-yl}-N-methyl-2-phenyl-acetamide (enantiomer 1);
2-{4-[2-(4-methoxy-phenyl)-ethyl]-2,3-dimethyl-6,7-dihydro-4H-thieno[3,2-c]pyridin-5-yl}-N-methyl-2-phenyl-acetamide (enantiomer 2);
2-{2-chloro-4-[2-(4-methoxy-phenyl)-ethyl]-6,7-dihydro-4H-thieno[3,2-c]pyridin-5-yl}-N-methyl -2-phenyl-acetamide (diastereoisomer 2); and
2-{2-chloro-4-[2-(4-methoxy-phenyl)-ethyl]-6,7-dihydro-4H-thieno[3,2-c]pyridin-5-yl}-N-methyl -2-phenyl-acetamide (enantiomer 1).

5. A compound of claim 2, wherein hetaryl is

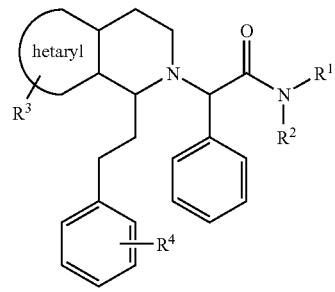

6. A compound of claim 5, which compound is
N-methyl-2-phenyl-2-{7-[2-(4-trifluoromethyl-phenyl)-ethyl]-4,7-dihydro-5H-thieno[2,3-c]pyridin-6-yl}-acetamide (diastereoisomer 2).

7. A pharmaceutical composition comprising a therapeutically effective amount of a compound of formula I

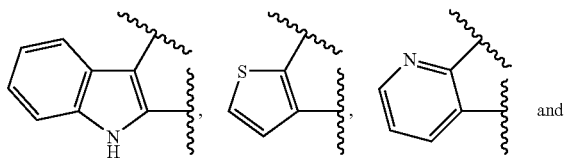

wherein
$R^1$ and $R^2$ are each independently hydrogen or lower alkyl;
$R^3$ is hydrogen, halogen, lower alkyl, lower alkyl substituted by halogen, lower alkoxy or lower alkoxy substituted by halogen;
$R^4$ is halogen, lower alkyl, lower alkyl substituted by halogen, lower alkoxy or lower alkoxy substituted by halogen;
hetaryl is a one or two ring-membered heteroaromatic ring system, connected to the carbon atoms of the piperidine group selected from the group consisting of

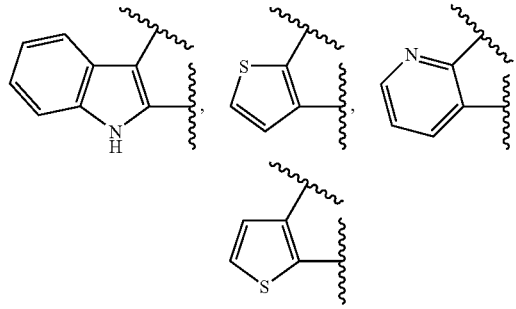

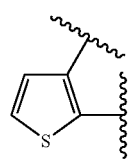

or a pharmaceutically suitable acid addition salt, enantiomer, racemate or diastereomeric mixture thereof,
and a pharmaceutically acceptable carrier.

8. A compound of claim 2, wherein hetaryl is

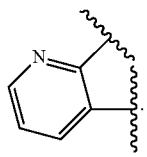

9. A compound of claim 1, selected from the group consisting of

2-{5-[2-(4-methoxy-phenyl)-ethyl]-7,8-dihydro-5H-[1,6]naphthyridin-6-yl}-N-methyl-2-phenyl-acetamide (diastereoisomer 2);

2-{5-[2-(4-methoxy-phenyl)-ethyl]-7,8-dihydro-5H-[1,6]naphthyridin-6-yl}-N-methyl-2-phenyl-acetamide (enantiomer 2);

2-{5-[2-(3-methoxy-phenyl)-ethyl]-7,8-dihydro-5H-[1,6]naphthyridin-6-yl}-N-methyl-2-phenyl-acetamide (diastereoisomer 2);

2-{5-[2-(3-methoxy-phenyl)-ethyl]-7,8-dihydro-5H-[1,6]naphthyridin-6-yl}-N-methyl-2-phenyl-acetamide (enantiomer 2);

N-methyl-2-phenyl-2-{5-[2-(4-trifluoromethyl-phenyl)-ethyl]-7,8-dihydro-5H-[1,6]naphthyridin-6-yl}-acetamide (diastereoisomer 2); and 2-{5-[2-(4-fluoro-phenyl)-ethyl]-7,8-dihydro-5H-[1,6]naphthyridin-6-yl}-N-methyl-2-phenyl-acetamide (enantiomer 2).

* * * * *

UNITED STATES PATENT AND TRADEMARK OFFICE
CERTIFICATE OF CORRECTION

| | | |
|---|---|---|
| PATENT NO. | : 8,067,598 B2 | Page 1 of 1 |
| APPLICATION NO. | : 12/056324 | |
| DATED | : November 29, 2011 | |
| INVENTOR(S) | : Gobbi et al. | |

It is certified that error appears in the above-identified patent and that said Letters Patent is hereby corrected as shown below:

TITLE PAGE,

Item (73) Assignee "Hoffman-La Roche Inc., Nutley, NJ (US)" should read
-- Hoffmann-La Roche Inc., Nutley, NJ (US) --.

Signed and Sealed this
Twenty-first Day of February, 2012

David J. Kappos
*Director of the United States Patent and Trademark Office*